United States Patent [19]

Bremer

[11] 4,225,465
[45] Sep. 30, 1980

[54] PRODUCTION OF MALEIC ANHYDRIDE FROM FOUR-CARBON HYDROCARBONS USING CATALYSTS PREPARED BY HYDROTHERMAL TECHNIQUES

[75] Inventor: Noel J. Bremer, Kent, Ohio

[73] Assignee: Standard Oil Company (Ohio), Ohio

[21] Appl. No.: 902,207

[22] Filed: May 2, 1978

Related U.S. Application Data

[63] Continuation-in-part of Ser. No. 801,950, May 31, 1977, Pat. No. 4,172,084.

[51] Int. Cl.$^2$ ............................................. B01J 27/14
[52] U.S. Cl. ...................................... 252/435; 252/437
[58] Field of Search ................................ 252/435, 437

[56] References Cited

U.S. PATENT DOCUMENTS

| | | | |
|---|---|---|---|
| 3,288,721 | 11/1966 | Kerr | 252/437 X |
| 3,541,143 | 11/1970 | Nakano et al. | 252/437 X |
| 3,867,411 | 2/1975 | Raffelson et al. | 250/346.75 |
| 3,915,892 | 10/1975 | Harrison | 252/437 X |
| 3,975,300 | 8/1976 | Burress | 252/435 |
| 3,977,998 | 8/1976 | Freerks et al. | 252/437 X |
| 3,985,775 | 10/1976 | Harrison | 252/437 X |
| 4,010,238 | 3/1977 | Shinaishi et al. | 252/437 X |
| 4,013,586 | 3/1977 | Dolan et al. | 252/437 |
| 4,016,105 | 4/1977 | Kerr | 252/437 |
| 4,018,709 | 4/1977 | Barone et al. | 252/435 |
| 4,062,873 | 12/1977 | Harrison | 252/435 X |
| 4,064,070 | 12/1977 | Harrison | 252/435 |
| 4,108,874 | 8/1978 | Moriya et al. | 252/437 X |
| 4,124,631 | 11/1978 | Hoyomi et al. | 252/437 X |
| 4,149,992 | 4/1979 | Mount et al. | 252/435 |

Primary Examiner—Delbert E. Gantz
Assistant Examiner—William G. Wright
Attorney, Agent, or Firm—Joseph G. Curatolo; Herbert D. Knudsen; Larry W. Evans

[57] ABSTRACT

Exceptionally reproducible catalysts comprising vanadium and phosphorus are obtained when an aqueous oxide slurry comprising vanadium, phosphorus and a mineral acid-free, inorganic reducing agent, which is capable of reducing the vanadium in the catalyst to a valence state below +5, is heated at an elevated temperature of at least 120° C. under autogenous pressure so that substantial evaporation of the water in said oxide slurry is prevented. Especially preferred catalysts comprise vanadium, phosphorus, uranium and oxygen. Catalysts prepared in accordance with the invention are especially desirable in the oxidation of n-butane, n-butenes, 1,3-butadiene or mixture thereof.

24 Claims, No Drawings

PRODUCTION OF MALEIC ANHYDRIDE FROM FOUR-CARBON HYDROCARBONS USING CATALYSTS PREPARED BY HYDROTHERMAL TECHNIQUES

REFERENCE TO RELATED APPLICATIONS

This is a continuation-in-part of our earlier application U.S. Ser. No. 801,950, filed May 31, 1977, now U.S. Pat. No. 4,172,084.

BACKGROUND OF THE INVENTION

1. Field of Invention

This invention relates to a method for preparing catalysts useful in the manufacture of dicarboxylic acid anhydride by the oxidation of hydrocarbons. More particularly, it is directed to the preparation of catalysts suitable for producing maleic anhydride from n-butane, n-butenes, 1,3-butadiene or mixture thereof.

2. Description of the Prior Art

The preparation of oxide catalysts comprising vanadium and phosphorus for use in a vapor phase oxidation of a hydrocarbon feed is known in the art. Various catalysts have been proposed wherein during the catalytic preparatory step, pentavalent vanadium in the catalyst is reduced to a valence state below $+5$ using a reducing agent. The conventional methods of preparing the catalysts involve combining a vanadium compound, a phosphorus compound, and when specified, promoter element compounds in an acidic reducing medium under conditions which will provide vanadium in a valence state below $+5$ to form a catalyst precursor, thermally convertible to an oxide or an oxide complex catalyst; and calcining the catalyst precursor at temperature of about 350° C. to about 600° C. for at least two hours. The reducing agents employed are usually solutions of mineral acids, particularly hydrochloric acid and phosphorous acid, or organic reducing agents, especially oxalic acid. For example, U.S. Pat. No. 3,985,775 to Harrison, et al. discloses the oxidation of n-butane using a mixed vanadium-phosphorus catalyst which is prepared by dissolving vanadium pentoxide in concentrated hydrochloric acid and adding 85% phosphoric acid to the resulting solution to yield a phosphorus to vanadium ratio of 0.5:1.0 (preferably 1.2:1.0). The resulting solution is then concentrated by heating to give a 50% solid aqueous slurry and then dried to constant weight at 150° C.; the dihydrate produced is preferably in or converted into, particulate form for processing through the subsequent phase transition. U.S. Pat. No. 3,975,300 to Burress, et al. teaches the use of organic reducing agents, such as glycol, sucrose, ethylene glycol, and propylene glycol, in the preparation of vanadium-phosphorus complex catalysts. U.S. Pat. No. 4,002,650 to Bremer, et al. discloses the oxidation of n-butane using a catalyst of the formula of $V_{0.5-3}P_{0.5-3}U_{0.1-0.5}O_x$. The preferred preparation of the catalyst involves refluxing a mixture of vanadium pentoxide, concentrated hydrochloric acid, and uranyl acetate. To this mixture is added 85% phosphoric acid. The mixture is evaporated at atmospheric pressure, dried at 110° C. and activated by heating in an air flow at 482° C. for 16 hours. U.S. Pat. No. 3,888,886 to Young, et al. discloses the oxidation of n-butane using a vanadium-phosphorus-oxygen complex catalyst having a phosphorus:vanadium atomic ratio of 0.5:2, promoted or modified with certain transition metals, preferably zirconium, chromium, iron or hafnium. These catalysts are prepared by refluxing a reaction mixture of vanadium oxide, phosphoric acid, a hydrogen halide (usually hydrochloric acid) and a specified promoter metal compound. U.S. Pat. No. 4,018,709 discloses the vapor phase oxidation of 4-carbon n-hydrocarbons using catalysts containing vanadium, phosphorus, uranium or tungsten or a mixture of elements from zinc, chromium, uranium, tungsten, cadmium, nickel, boron and silicon. Preferably, the catalytic complex also contains an alkali metal or an alkaline earth metal, especially lithium, sodium, magnesium or barium, as active components. Catalysts are prepared in a 37%-hydrochloric acid solution. U.S. Pat. No. 3,980,585 to Kerr, et al. discloses the preparation of maleic anhydride from n-4C hydrocarbons in the presence of a catalyst containing vanadium, phosphorus, copper, oxygen, tellurium or a mixture of tellurium and hafnium or uranium. The process may also be conducted in the presence of a catalyst containing vanadium, phosphorus, copper, at least one of Te, Zr, Ni, Ce, W, Pd, Ag, Mn, Cr, Zn, Mo, Re, Sm, La, Hf, Ta, Th, Co, U, on and optionally an element from Groups IA or IIA. This patent exemplifies the use of oxalic acid in the preparation. U.S. Pat. No. 4,016,105 teaches the preparation of a V-P complex catalyst in an aqueous phosphoric acid solution using an organic acid or aldehyde and secondary alcohol as reducing agents; U.S. Pat. No. 4,062,873 discloses use of isobutyl alcohol and benzyl alcohol as reducing agents.

U.S. Pat. No. 3,907,835 to Kobylinski discloses the production of maleic anhydride from benzene, butene, butadiene, butanol-2 or pentanol-2 using a catalyst of the formula $U_{1-3}O_{6-16}P_{1-4}H_{0-4}$, and optionally containing vanadium. Where vanadium is present, the catalyst is prepared by mixing an anhydrous uranium salt with vanadyl oxalate (vanadium to uranium is 0.1:1 to 0.1:2) and adding enough concentrated phosphoric acid to give a uranium to phosphorus ratio of 0.2:1 to 2:1 molar ratio and phosphorus to oxygen ratio of 0.1:1 to 0.35:1 to precipitate the catalyst which is dried at 29° C.–140° C. and heated to 420° C.–500° C. The vanadium content of this catalyst is preferably 6 to 40 weight percent. The anhydrous uranium salt is especially a phosphate prepared by addition of a base to an aqueous solution of uranyl nitrate in concentrated phosphoric acid and drying and calcining to obtain catalytic precipitate.

Of particular interest is U.S. Pat. No. 3,977,998 to Freerks, et al., which discloses the oxidation of n-butane in the presence of a phosphorus-vanadium-oxygen complex catalyst, wherein the phosphorus to vanadium atom ratio is 1-2:2-1, the catalyst being prepared by (a) contacting a vanadium compound and a phosphorus compound in acid solution containing a reducing agent under conditions which will provide at least 50 atom percent of vanadium in tetravalent form; (b) separating the prepared catalyst precursor and (c) calcining the catalyst precursor at 350° C.–660° C. for at least two hours, the improvement comprising that the calcination is effected in an inert atmosphere. The reducing agent may be a hydrogen halide acid or oxalic acid, but is preferably a mixture of phosphoric acid containing sufficient phosphorus acid to reduce $V^{+5}$. Preferred catalyst precursors have a phosphorus to vanadium atom ratio of 1:1 to 1.5:1, especially 1:1 to 1.2:1. Exemplified in this patent is the use of a catalyst of the formula $P_{1.05}V_1O_x$ prepared by digesting vanadium pentoxide in a mixture of water, 85% phosphoric acid and 99.4% phosphorus acid. This mixture was heated to 100° C. in an autoclave which was then sealed; the mixture was heated for 3 hours at 145° C. and solid catalyst precursor was collected and slurried in 20 weight percent water. Viscous putty was extruded through a 0.35 cm. diameter die and cut into pellets, then air-dried and heated to 125° C. Pellets were heated in a muffle furnace to 350° C. for one hour and then to 375° C. an additional hour. The air in the furnace was replaced by nitrogen gas, and the temperature was raised to 500° C. over a five hour period. The catalyst was cooled rapidly to room temperature under nitrogen gas and possessed a 93 atom percent of vanadium as $V^{+4}$.

U.S. Pat. No. 3,907,707 discloses preparing a vanadium-containing catalyst wherein a tetravalent vanadium compound is provided from a pentavalent vanadium compound, comprising contacting the pentavalent vanadium compound with a trivalent phosphorus compound. In accordance with the present invention, catalysts are prepared in the absence of compounds containing trivalent phosphorus.

All of these teachings in the prior art have failed to achieve the desirable results obtained by the use of the present invention. The activity and quality of catalysts prepared using conventional prior art techniques are diverse because catalysts containing vanadium and phosphorus are especially sensitive to their mode of preparation. Using the present invention, reproducible catalysts of enhanced activity and selectivity are obtained.

SUMMARY OF THE INVENTION

It is an object of the present invention to provide an improved process for the vapor phase oxidation of n-butane, n-butenes, 1,3-butadiene or mixture thereof to maleic anhydride.

It is a further object of this invention to provide a method for preparing a catalyst comprising oxides of vanadium and phosphorus.

In accordance with the present invention has been discovered a process for the preparation of maleic anhydride by the oxidation of n-butane, n-butene, 1,3-butadiene or mixture thereof with molecular oxygen in the vapor phase at a reaction temperature of 250° C. to 600° C. in the presence of a catalyst comprising the mixed oxides of vanadium and phosphorus, the improvement wherein the catalyst is prepared by (a) forming an aqueous oxide slurry of a vanadium compound containing pentavalent vanadium and a mineral acid-free, inorganic reducing agent capable of reducing said pentavalent vanadium to a valence state below +5;

(b) admixing a phosphorus compound containing pentavalent phosphorus with said aqueous slurry of step (a);

(c) heating said aqueous slurry of step (b) at a temperature of at least 120° C. under autogenous pressure so that substantial evaporation of the water in said slurry is prevented;

(d) removing the water from the slurry of step (c) to form a dried catalyst; and (e) calcining the dried catalyst at a temperature of 250° C. to 600° C. in the presence of an oxygen-containing gas.

Effective results are observed when the catalyst is based solely upon vanadium, phosphorus and oxygen but, from the standpoint of optimum benefits and catalyst effectiveness, it is preferred that uranium be incorporated in the catalyst to enhance the activity of the base catalytic system. Additional promoters may be selected from the group consisting of elements of Groups I (B) through VI (B), VIII, lanthanides, actinides, and I (A) through VI (A), excluding the elements H, N, O, C, Fr, Ra, and Po. Catalysts of particular interest consist of the elements vanadium, phosphorus, uranium, oxygen, and optionally at least one of Ta, Ce, Cr, Mn, Co, Cu, Sb, Fe, Bi, W, Mo, Hf, Zr, Th, an alkaline earth metal and an alkali metal. Of these promoter elements, Ta, Ce, Mn, Co, Sb, Fe, Bi, W and Mo are preferred. Excellent results may be obtained using catalysts having a phosphorus to vanadium atom ratio of 0.1:10 to 10:0.1. Especially desirable results are observed using catalysts wherein the phosphorus to vanadium atom ratio is 0.5:3 to 3:0.5.

The method employed in preparing the catalyst is critical to the process for producing maleic anhydride. Maximum conversions of maleic anhydride are obtained where the starting material is n-butane or n-butenes. Essentially all the product produced in this process is maleic anhydride with only minor amounts of lower acids being detected.

The method employed in preparing the catalyst departs from the classical procedures involving reducing the vanadium in the catalyst to a valence state below +5 using an acid, such as a hydrogen halide acid or an organic acid, in particular hydrochloric acid or oxalic acid, as the reducing agent. By the preferred procedure of the invention a compound containing pentavalent vanadium in an aqueous suspension is pre-reduced in a controlled manner so that at least some of the vanadium is reduced to a valence state below +5 before the compound containing pentavalent vanadium is mixed with a compound containing pentavalent phosphorus, followed by heating the aqueous mixture at an elevated temperature of at least 120° C., preferably 120° C. to 250° C., under autogenous pressure. Suitable vanadium compounds containing pentavalent vanadium include: vanadium pentoxide or vanadium salts, such as ammonium metavanadate, and vanadium oxytrihalides, however vanadium pentoxide is preferred. Suitable phosphorus compounds containing pentavalent phosphorus include: phosphoric acid, phosphorus pentoxide, or phosphorus perhalides, such as phosphorus pentachloride, however, phosphoric acid and phosphorus pentoxide are preferred.

Representative examples of suitable reducing agents include hydrazine, hydrazine hydrate, ammonia, hydrides, such as sodium borohydride, or finely divided or colloidal metals of molybdenum, tungsten, magnesium, aluminum, or nickel. When powdered metals are employed, the amount of metal reacted ranges from 0.01 to 5 atoms per mole of the pentavalent vanadium present. It is to be understood that in accordance with the present invention suitable reducing agents do not include compounds containing trivalent phosphorus or inorganic acids, such as phosphorus acid and hydrogen halide acids, or organic reducing agents, such as oxalic acid, citric acid, formic acid, ascorbic acid, malic acid, glycol, sucrose, ethylene glycol, and propylene glycol, aldehydes, such as formaldehyde and acetaldehyde, or alcohols, such as ethanol, isobutyl alcohol or benzyl alcohol.

An especially preferred procedure of the invention involves refluxing an aqueous slurry of a vanadium compound containing pentavalent vanadium, a reducing agent, and at least one compound containing the respective promoter elements for a period of ½ hour to 16 hours. The amount of water present in solution can range from 500 to 2000 mls. per mole of vanadium present. A compound containing pentavalent phosphorus is digested in the aqueous slurry containing reduced vanadium, and the resulting aqueous slurry is heated at a temperature of at least 120° C. under autogenous pressure. Preferredly, the resulting aqueous slurry is heated at a temperature of 120° C. to 300° C. under autogenous pressure of 15 to 1300 p.s.i.g. Especially preferred is to heat the slurry at a temperature of 130° C. to 240° C. under autogenous pressure of 20 to 500 p.s.i.g.

Heating the aqueous mixture at elevated temperatures under autogenous pressure is critical to the invention. It is hypothesized that the problem encountered in reproducing catalysts using traditional low temperature preparatory routes is attributed to the condensation to polyphosphates caused by the evaporation of water and possibly catalyzed by the vanadium. When the catalysts of the invention were analyzed by X-ray defraction spectroscopy, it was observed that the formation of condensed polyphosphates were inhibited.

A reproducible method of combining the catalytic ingredients comprises:

(a) refluxing an aqueous oxide slurry containing vanadium pentoxide and a mineral acid-free, inorganic reducing agent capable of reducing the vanadium in the vanadium pentoxide to a valence state below +5 to obtain an aqueous slurry containing reduced vanadium;

(b) admixing phosphoric acid with said aqueous slurry containing reduced vanadium;

(c) autoclaving the aqueous slurry of step (b) at a temperature of 120° C. to 300° C. under autogenous pressure of 15 to 1500 p.s.i.g. so as to retain substantially all of the water content in the slurry;

(d) removing the water from the slurry of step (c) to form a dried catalyst; and (e) calcining said dried catalyst at a temperature of 250° C. to 600° C. in the presence of an oxygen-containing gas.

Although preferably the compound containing pentavalent vanadium is pre-reduced before reaction with phosphoric acid, beneficial results are achieved by reacting the vanadium pentoxide with phosphoric acid followed by reaction with the reducing agent, or by reacting the three components together followed by the addition of compounds containing the respective promoter elements. However, superior results are observed when the compounds containing the respective promoter elements are added to the aqueous slurry containing reduced vanadium immediately preceding the addition of phosphoric acid.

A catalyst prepared in accordance with the present invention whereby the most favorable results are achieved comprise vanadium, phosphorus, uranium and oxygen. This catalyst is described by the formula

wherein
a and b are 1 to 10;
c is 0.01 to 5;
x is the number of oxygens required to satisfy the valence requirements of the other elements present;
and wherein
said catalyst optionally contains at least one element selected from the group consisting of tantalum, cerium, chromium, manganese, cobalt, copper, antimony, iron, bismuth, tungsten, molybdenum and sulfur.

An optional promoter may be present in the catalyst in an atomic range of 0.01 to 1. Especially desirable results are obtained using catalysts wherein a and b are 0.5 to 3, catalysts wherein c is 0.1 to 0.5, and catalysts wherein tungsten is present in the catalyst in an atomic range of 0.01 to 5.

The catalyst is activated by calcining it in air or an oxygen-containing gas at a temperature of 250° C. to 600° C. for a period of up to 5 hours or more. A preferred activation of the catalyst is accomplished by passing a mixture of steam and air or air alone over the catalyst at a temperature of about 300° C. to 500° C. for a period of about 1 to 5 hours. The hydrocarbon reacted may be n-butane, n-butenes, 1,3-butadiene, or a mixture thereof. Preferred is the use of n-butane or a mixture of hydrocarbons that are produced in refinery streams. The molecular oxygen is most conveniently added as air, but synthetic streams containing molecular oxygen are also suitable. In addition to the hydrocarbon and molecular oxygen, other gases may be added to the reactant feed. For example, steam or nitrogen could be added to the reactants.

The ratio of the reactants may vary widely and are not critical. The ratio of the hydrocarbon to molecular oxygen may range from about 2 to about 30 moles of oxygen per mole of hydrocarbon. Preferred oxygen ratios are about 4 to about 20 moles per mole of hydrocarbon.

The reaction temperature may vary widely and is dependent upon the particular hydrocarbon and catalyst employed. Normally, temperatures of about 250° C. to about 600° C. are employed with temperatures of 350° C. to 500° C. being preferred.

The catalyst may be used alone or a support could be employed. Suitable supports include silica, alumina, Alundum ®, silicon carbide, boron phosphate, zirconia, and the like. The catalysts are conveniently used in a fixed-bed reactor using tablets, pellets or the like, or in a fluid-bed reactor using a catalyst preferably having a particle size of less than about 300 microns. The contact time may be as low as a fraction of a second or as high as 50 seconds. The reaction may be conducted at atmospheric, superatmospheric or subatmospheric pressure.

SPECIFIC EMBODIMENTS

Examples 1 to 67 and Comparative Examples 1 to 47

Preparation of Maleic Anhydride Using Catalysts Prepared by the The Invention Compare with Performance of Catalysts Prepared by Other Techniques A 20 cc. fixed-bed reactor was constructed equipped with a split-feed induction system. Catalysts prepared as described below were charged to the reactor and heated to the reaction temperature and n-butane was reacted with air in the proportions specified in TABLES I to V at an apparent contact time of 1 to 2 seconds. n-Butane was premixed with partial air in a 30 cm.×41 cm. packed tube as the mixture was regulated to a splitter allowing only a slip stream to flow to the reactor. Liquid product was recovered in aqueous scrubbers and titrated for total acid. Product samples were found to be pure maleic anhydride. Off-gas analyses for 4-carbon hydrocarbons, carbon monoxide, carbon dioxide, and oxygen were determined using a Carle A.G.C. III equipped with a heated column oven, wherein the column system consisted of molecular seives and sebacyl chloride on chromosorb.

Examples 1 to 5 and Comparative Examples 1 to 6

Examples 1 to 4

A catalyst of the formula $V_{1.0}P_{1.15}U_{0.20}O_x + W\%_{0.166}$ was prepared as follows:

Example 1

Part A: An aqueous slurry was prepared consisting of 36.37 grams of vanadium pentoxide, 22.4 grams of black uranium oxide, and 50 mls. of distilled water. This mixture was wet-ball milled for 3 hours to ensure intimate mixing and a reasonable degree of dispersion. After separation, the slurry was suspended in 600 mls. of distilled water; 12.26 grams of tungsten metal having a particle size of less than 10 microns were added and the mixture was refluxed with stirring for 2.5 hours at ambient pressures. The color of the slurry changed from yellowish-green to black. This aqueous slurry was cooled and then 53.0 grams of 85% phosphoric acid were added. The resulting aqueous slurry was charged to an autoclave, the autoclave was sealed, and the mixture was heated with stirring at 180° C. for about 1 hour under an autogenous pressure of 90 p.s.i.g. Heating was terminated and the contents of the autoclave, a grayish-green paste, was cooled and washed into a beaker with 200 mls. of distilled water. The slurry was evaporated with stirring at 100° C. for 20–24 hours. The resulting mixture was damp and light green in color. This material was dried overnight at 110° C. The dried catalyst, which was hard, dense and green-gray in color, was calcined at 482° C. in air for 2 hours. The final product was hard, dense and medium green in appearance.

Part B: A duplicate catalyst was prepared using the same techniques described in Part A, except a different autoclave heater and variac were employed. Following the addition of 85% phosphoric acid, the resulting aqueous slurry was charged to an autoclave, the autoclave was sealed and the mixture was heated with stirring at 180° C. for about 1.5 hours under an autogenous pressure of 120 p.s.i.g. Heating was terminated and the contents of the autoclave were stirred for two days. The cooled contents of the autoclave, having the same appearance as the material in Part A, was washed into a 2-liter beaker with enough distilled water to increase the volume to 900 cc. This solution was boiled to a thick green-gray paste, dried at 170° C. for 24 hours, was hard and greenish-gray in color, and the resulting material was calcined at 482° C. for 2 hours in air. The final product was medium green in color and hard.

EXAMPLE 2

37.36 grams of vanadium pentoxide and 22.4 grams of black uranium oxide were wet ball-milled for 2.5 hours in 50 mls. of distilled water. After separation, slurry was suspended in 600 mls. of distilled water and 12.26 grams of tungsten metal powder were added. The mixture was refluxed with stirring for 2 hours to achieve reduction, 53 grams of 85% phosphoric acid were added, and the resulting aqueous mixture was placed in an autoclave. The autoclave was sealed, and the mixture was heated with stirring at 135° C. for one hour under an autogenous pressure of 30 p.s.i.g. The contents of the autoclave were permitted to cool, boiled to a thick paste, dried in an oven at 110° C. for 12 hours, and calcined at 482° C. in air for 2 hours. The final product was hard, dense, and dark green in appearance.

EXAMPLE 3

36.37 grams of vanadium pentoxide were wet ball-milled for 2 hours in 50 mls. of distilled water. After separation, the slurry was suspended in 600 mls. of distilled water and 12.26 grams of tungsten metal powder were added; the aqueous slurry was refluxed for 2 hours. To this slurry were added 33.93 grams of uranyl acetate and 53.0 grams of 85% phosphoric acid. This mixture was placed in an autoclave, the autoclave was sealed, and the contents were heated with stirring at 135° C. under autogenous pressure of 30 p.s.i.g. for 1 hour. The contents were permitted to cool and the resulting material was a deep green heavy solution with some suspended material. This material was washed into a beaker and boiled to a thick paste, dried at 110° C., and calcined at 482° C. in air for 2 hours. The final product was hard, but slightly porous.

EXAMPLE 4

36.37 grams of vanadium pentoxide, 22.40 grams of black uranium oxide and 12.76 grams of powdered tungsten metal were wet ball-milled for 3 hours in 50 mls. of distilled water; this mixture was refluxed in 600 mls. of distilled water. The color of the reduced slurry was black, compared with the color of the slurry of Example 1, Parts A and B. To this slurry were added 53 grams of 85% phosphoric acid. The mixture was placed in an autoclave, the autoclave was sealed, and the contents were heated with stirring at 215° C. under autogenous pressure of 225 p.s.i.g. for ½ hour; heating was continued at 235° C. under autogenous pressure of 400 p.s.i.g. The contents were permitted to cool, evaporated to dryness in an oven at 110° C. The resulting product was calcined at 482° C. in air for 2 hours. The final product was hard, brittle, an olive green in appearance.

Comparative Examples 1 and 2

Catalysts were prepared using (1) hydrochloric acid as a reducing agent or (2) oxalic acid as a reducing agent.

Comparative Example 1

$V_{1.0}P_{1.15}U_{0.20}O_x$ (Vanadium reduced with hydrochloric acid)

Part A: 33.0 grams of vanadium pentoxide were digested in 440 mls. of concentrated hydrochloric acid and refluxed with stirring for 1.5 hours. Color gradually changed from brown to blue. To this reflux slurry were added 31.0 grams of uranyl acetate dihydrate and the resulting mixture was refluxed an additional hour. 49.0 grams of 85% phosphoric acid were added and the mixture was refluxed 2.0 hours. The total mixture was evaporated over a 3.5 hour period and dried in an oven at 110° C. overnight. The catalyst was ground and screened to give a 10×30 mesh fraction and was activated by calcining in an air flow at 260° C. for 3 hours. The final product was hard, and dark green in appearance.

Part B: A duplicate catalyst was prepared in the same manner described in Part A, except after vanadium pentoxide was digested in hydrochloric acid, the mixture was refluxed for 2.0 hours; total mixture was evaporated over 1.5 hour period; dried in an oven an additional 4 hours at 125° C.; and calcined in air at 288° C.

for 3 hours. The final product was green with gold flaws in appearance.

Part C: A second duplicate catalyst was prepared in the same manner described in Part A.

Comparative Example 2

$$V_{1.0}P_{3.2}U_{0.20}O_x$$

(Vanadium reduced with oxalic acid)

This catalyst was prepared as follows: 36.37 grams of vanadium pentoxide were dispersed in 200 mls. of distilled water and stirred with a magnetic bar at 80° C. To this aqueous solution, 95 grams of oxalic acid were slowly added. Gas evolved and the solution gradually darkened to deep blue. 33.93 grams of uranyl acetate dihydrate were added and the resulting mixture was refluxed for ½ hour, then 47.58 grams of 85% phosphoric acid were added. Refluxing continued for 2 hours. The mixture was permitted to cool to room temperature overnight. Liquors were removed, and the remainder was evaporated to a thick paste, dried in an oven for 4 days, and calcined at 288° C. in air for 3 hours. Final product was "blown" and light blue-green in appearance.

Comparative Examples 3 to 5

A catalyst of the formula $V_{1.0}P_{1.15}U_{0.20}O_x + W^o{}_{0.166}$ was prepared by (3) employing a low temperature preparation of an aqueous slurry and evaporating the slurry over a nitrogen stream, (4) a low temperature preparation of an aqueous slurry, and (5) autoclaving the catalytic material at 110° C.

Comparative Example 3

33.37 grams of vanadium pentoxide and 22.40 grams of black uranium oxide were wet ball-milled in 50 mls. of distilled water overnight. This mixture was slurried into a beaker with 800 mls. of distilled water, 12.26 grams of powdered tungsten metal were added, and mixture was refluxed an additional 2.5 hours at 71° C. To this mixture were slowly added 53 grams of 85% phosphoric acid. The color of the slurry changed from black to medium green. The temperature was stabilized at 66° C. for 1 hour, then evaporation was initiated in the presence of a nitrogen stream at 57° C. Evaporation was accomplished in 2 days, and temperature was increased to 77° C. The resulting product was dried in an oven at 110° C. and calcined in air at 482° C. for 2 hours. The final product was porous and green in appearance.

Comparative Example 4

Part A: 36.37 grams of vanadium pentoxide and 22.40 grams of black uranium oxide were wet ball-milled in 50 mls. of distilled water overnight. The next day, enough distilled water was added to bring the volume up to 600 mls., then 12.26 grams powdered tungsten metal were added. This mixture was heated at 103° C., and was black in appearance. After 1½ hours elapsed, temperature decreased to 55°-65° C. In about ½ hour, 53 grams of 85% phosphoric acid were added at 65° C. in addition to 100-150 mls. distilled water. The color of the slurry changed to green, however, some solubilization occurred, and in about 20 minutes the slurry was black-green in appearance. The next morning, the slurry was evaporated at 75° C. and was shrunken and blue-green in appearance.

Part B: A duplicate catalyst of Part A was prepared in the same manner described above, except the mixture containing vanadium pentoxide, black uranium oxide, and tungsten metal was heated at 88° C., and was green in appearance; after 85% phosphoric acid was added, the color of the slurry was medium green; and after evaporation the dried catalyst was swelled, having the appearance of being dry only on the surface, and light brownish-green in appearance.

Comparative Example 5

Part A: 36.37 grams of vanadium pentoxide and 22.40 grams of black uranium oxide were wet ball-milled in 50 mls. of distilled water for 2 hours. To this aqueous slurry were added 12.26 grams of tungsten metal powder and the mixture was refluxed for 2 hours. Upon cooling overnight, the slurry was very dark green in appearance with a heavy dark green-black residue. 53.0 grams of 85% phosphoric acid were added and the mixture was placed in an autoclave, the autoclave was sealed, and the contents were heated with stirring at 110° C. for 1 hour. Upon cooling, the thickened material was dark green in appearance. This material was boiled to a thick paste, dried at 110° C. and calcined at 482° C. in air for 2.5 hours. The final product was brittle, slightly soft and dark green in appearance.

Part B: 40 grams of vanadium pentoxide were placed in a porcelain crucible, heated on a Fisher burner until dissolved, and poured into 600 mls. of rapidly stirred distilled water, resulting in a deep red colloid. The colloid was heated to boiling and 22.4 grams of black uranium oxide, having been wet ball-milled 3 hours, were added, and within minutes the solution thickened and became green in appearance. The slurry thickened considerably when 12.26 grams of powdered tungsten metal were added. The slurry subsequently loosened and the color changed to darker green. This mixture was refluxed for two hours, charged to an autoclave, the autoclave was sealed, and the contents were heated for 2 hours at 110° C. under 15 p.s.i.g. autogenous pressure. The discharged slurry was gray in appearance. This material was evaporated to dryness and calcined at 488° C. in air for 2 hours. The final product was hard, homogenous, and deep green in appearance.

Comparative Example 6

A catalyst of the formula $V_{1.0}P_{1.0}U_{0.20}O_x$ was prepared by preforming a $V_2O_5$-$P_2O_5$ complex, then reducing $V^{+5}$ as follows: A first solution was prepared consisting of 11.6 grams of $NH_4VO_3$ and 600 mls. of distilled water. A second solution was prepared consisting of 23 grams of $NH_4H_2PO_4$ and 150 mls. of distilled water. The second solution was added to the first, and the color of the first solution changed from yellow to deep orange. To this mixture, concentrated nitric acid was added dropwise until the mixture was red in appearance. The mixture was refluxed and 31.0 grams of uranyl acetate dihydrate were added resulting in a deep orange gellation. The mixture was allowed to stand overnight and the next day enough distilled water was added to bring the volume up to 500 mls. Hydrazine hydrate was added dropwise until the color of the slurry changed from red to green to gray. The resulting mixture was refluxed for 5 hours, boiled to dryness, dried in an oven overnight at 105° C., and calcined for 2 hours in air at 488° C. The final product was light, fluffy, and blue-green-gray in appearance.

Example 5 and Comparative Examples 7 to 9

Example 5

A catalyst of the formula $V_{1.0}P_{1.15}O_x + W^o{}_{0.166}$ was prepared as follows:

An aqueous slurry was prepared consisting of 36.37 grams of vanadium pentoxide, 12.26 grams of powdered tungsten metal, and 600 mls. of distilled water. The slurry was refluxed for 2.5 hours and permitted to cool; 53 grams of 85% phosphoric acid was added. The slurry was charged to an autoclave. The autoclave was sealed, and the contents were heated at 135° C. under 25-30 p.s.i.g. autogenous pressure. Heating was terminated and the contents were washed into a beaker with 200 mls. of distilled water. The resulting mixture was boiled to a thick paste, dried overnight in an oven at 110° C., and calcined at 488° C. in air for 2 hours. The final product was hard, dense and deep green in appearance.

Comparative Examples 7 and 8

A catalyst of the formula $V_{1.0}P_{1.15}O_x$ was prepared using (7) hydrochloric acid digestion. A second catalyst of the formula $V_{1.0}P_{1.15}O_x + W^o{}_{0.166}$ was prepared by (8) evaporation of the catalytic material on a steam bath.

Comparative Example 7

33.6 grams of vanadium pentoxide were digested in 437.5 mls. of hydrochloric acid and refluxed for 3-4 hours. To this mixture were added 48.65 grams of 85% phosphoric acid and refluxing continued an additional 6 hours. The resulting mixture was evaporated to dryness, and dried overnight at 110° C. The product consisted of two distinct crystalline phases: one was blue and another was gold in appearance. Calcination was conducted for 1 hour at 360° C. in air.

Comparative Example 8

Part A: A slurry was prepared consisting of 36.37 grams of vanadium pentoxide, 12.26 grams of powdered tungsten metal and 600 mls. of water and refluxed for 2.25 hours. 53 grams of 85% phosphoric acid were added and refluxing continued an additional 1.5 hours. This mixture was evaporated overnight over a steam bath, and dried in an oven over the weekend. The material was black and glassy in appearance and was calcined for 2 hours at 488° C. in air.

Part B: A duplicate catalyst was prepared in the same manner described in Part A. After calcination, the final product was deep green-brown in appearance.

Comparative Example 9

A catalyst of the formula $V_{1.0}P_{1.0}O_5$ was prepared by preforming a $V_2O_5$-$P_2O_5$ complex as follows: 50 grams of vanadium pentoxide were ball-milled with 39 grams of phosphorus pentoxide and heated at 850° C. in an oven overnight. The next day, temperature was incrementally decreased at a rate of 40° C./hour until a temperature of 650° C. was reached. Heating was terminated, and mixture was cooled. The product had the appearance of being hard, glassy, and green-black in color, covered with small green-yellow crystals.

Examples 6 to 21

Preparation of Various Catalysts of the Invention

Examples 6 to 17

Various catalysts of the invention having the general formula $V_{1.0}P_{1.15}U_{0.20}X_{0.05}O_x + W^o{}_{0.166}$ were prepared using the same procedure described in Examples 1 to 4, except a compound containing an element delineated by X was added in the preparation of the catalyst immediately preceding the addition of 85% phosphoric acid. The amount of compound containing the X component appears in the following Table.

| X = | Compound | Amount, Grams | Autoclave Conditions Temp. °C. | Pressure, p.s.i.g. |
|---|---|---|---|---|
| Ta | tantalum oxide | 4.42 | 135 | 30 |
| Ce | cerium acetate monohydrate | 6.88 | 160 | 50 |
| Cr | chromium nitrate monohydrate | 8.00 | 130 | 28 |
| Mn | manganese chloride tetrahydrate | 3.96 | 130 | 28 |
| Co | cobaltous acetate tetrahydrate | 4.98 | 140 | 40 |
| Cu | copper acetate monohydrate | 3.99 | 140 | 35 |
| Sb | antimony triacetate | 5.98 | 140 | 40 |
| Fe | ferric nitrate nonahydrate | 8.08 | 125-135 | 25-30 |
| Bi | bismuth pentahydrate | 8.42 | 120-125 | 20 |
| W | tungsten trioxide | 6.42 | 130 | 25-28 |
| Mo | molybdenum trioxide | 2.88 | 130 | 27 |
| (Misch metal oxide) | rare earth mixture consisting essentially of oxides of Ce, Dy, La and Nd | 3.44 | 135 | 20 |

Examples 18 to 20

Various catalysts of the invention having the general formula $V_{1.0}P_{1.15}U_{0.20}X_{0.02}O_x + W^o{}_{0.166}$ were prepared using the same procedure described in Examples 6 to 17. The amount of compound containing the X component appears in the Table below:

| X = | Compound | Amount, Grams | Autoclave Conditions Temp. °C. | Pressure, p.s.i.g. |
|---|---|---|---|---|
| K | potassium sulfate | 0.69 | 160 | 75 |
| Li | lithium hydroxide monohydrate | 0.34 | 140 | 40 |
| Ga | gallium trichloride | 1.41 | 130 | 26 |

Examples 21 to 64 and Comparative Examples 10 to 47

Examples 21 to 39 and Comparative Examples 10 to 42

Reaction of n-Butane Using Catalysts Prepared by Invention Compared With Catalysts Prepared by Other Methods Performance of the catalysts prepared in Examples 1 to 4 is exemplified in Examples 21 to 36. Generally, there was good reproducibility even with diverse temperature variations during preparation. Each preparation yielded at least 40% per pass conversion to maleic anhydride and the overall activities and selectivities were consistently uniform.

Performance of the catalyst of Comparative Example 1 prepared by hydrochloric acid digestion is exemplified in Comparative Examples 10 to 26. Comparative Examples 10 to 13 show the performance of the best and original catalyst prepared by this technique. A slight increase in acid conversion occurred during 200 hours on stream, and the catalyst generally yielded 41-42% per pass conversion to maleic anhydride. The reducing agent for this catalyst was concentrated hydrochloric acid. Digestion of $V_2O_5$ in this medium resulted in reductive chlorination of vanadium to $VOCl_2$. Comparative Examples 14 to 19 show the performance of an exact duplicate, which deactivated dramatically with time on stream. After 96 hours, pure butane was purged over the catalyst at 482° C. for 15 minutes, and then the catalyst was put on stream with normal air mixture. Initially, this increased the selectivity from 30 to 50%. However, within 30 hours the maleic anhydride conversion had dropped from 38% to 29%. Comparative Examples 20 to 26 show the performance of a second duplicate. After 99 hours on stream, a feed of 1 n-butane/50 steam/50 air was fed over catalyst for one hour.

The performance of the catalyst prepared in Comparative Example 2 using oxalic acid is shown in Comparative Example 27. This catalyst was essentially inactive with a 6.8% per pass conversion at 478° C., however, oxalic acid reduced catalysts containing less phosphorus were completely inactive.

The performance of catalysts of Comparative Examples 3 and 4 are exemplified in Comparative Examples 28 to 30. Generally, these catalysts were ineffective in the oxidation of n-butane. Catalysts of Comparative Example 5, prepared in an autoclave at 110° C., are shown in Comparative Examples 31 to 35. The performance of the catalyst of Comparative Example 6 is exemplified in Comparative Example 36. The results reveal that this catalyst deactivates with time on stream.

The results are shown in TABLE I. The results are stated as follows:

$$\text{Per Pass Conversion} = \frac{\text{Moles of Total Acid Calculated As Maleic Anhydride}}{\text{Moles of Hydrocarbon Fed}} \times 100$$

Performance of the catalyst prepared in Example 5 is exemplified in Examples 37 to 39 compared with performance of catalysts prepared in Comparative Examples 7 to 9, exemplified in Comparative Examples 32 to 42. Results of these experiments appear in TABLE II.

TABLE I

Reaction of n-Butane Using Catalysts Prepared by Invention Compared with Catalysts Prepared by Other Methods

| Example | Catalyst | Temp. °C. Bath | Temp. °C. Bed | Molar Feed Ratio Air/n-Butane | Hours on Stream | Per Pass Conversion, % TA* | Selectivity |
|---|---|---|---|---|---|---|---|
| 21 | $V_{1.0}P_{1.15}U_{0.20}O_x + W°_{0.166}$ (prepared in autoclave at 180° C.) | 491.7 | 505.6 | 98 | 4.0 | 36.1 | 36.6 |
| 22 | $V_{1.0}P_{1.15}U_{0.20}O_x + W°_{0.166}$ (prepared in autoclave at 180° C.) | 450 | 472.8 | 96 | 100.6 | 41.3 | 42.7 |
| 23 | $V_{1.0}P_{1.15}U_{0.20}O_x + W°_{0.166}$ (prepared in autoclave at 180° C.) | 445.6 | 466.1 | 91 | 120.5 | 42.6 | 45.3 |
| 24 | $V_{1.0}P_{1.15}U_{0.20}O_x + W°_{0.166}$ (prepared in autoclave at 180° C.) | 465.6 | 476.7 | 93 | 172.0 | 49.4 | 53.4 |
| 25 | $V_{1.0}P_{1.15}U_{0.20}O_x + W°_{0.166}$ (Duplicate) | 465.6 | 490.6 | 88.5 | 23.7 | 44.5 | 42.6 |
| 26 | $V_{1.0}P_{1.15}U_{0.20}O_x + W°_{0.166}$ (Duplicate) | 453.3 | 477.8 | 86.0 | 30.1 | 43.7 | 45.7 |
| 27 | $V_{1.0}P_{1.15}U_{0.20}O_x + W°_{0.166}$ (Duplicate) | 438.3 | 462.8 | 85.0 | 101.2 | 43.5 | 44.7 |
| 28 | $V_{1.0}P_{1.15}U_{0.20}O_x + W°_{0.166}$ (Prepared in autoclave at 135° C.) | 483.9 | 495 | 92 | 2.2 | 43.2 | 47.7 |
| 29 | $V_{1.0}P_{1.15}H_{0.20}O_x + W°_{0.166}$ (Prepared in autoclave at 135° C.) | 478.3 | 496.1 | 85 | 49.2 | 47.02 | 44.2 |
| 30 | $V_{1.0}P_{1.15}U_{0.20}O_x + W°_{0.166}$ (prepared in autoclave at 135° C.) | 469.4 | 487.8 | 93 | 145 | 45.4 | 44.9 |
| 31 | $V_{1.0}P_{1.15}U_{0.20}O_x + W°_{0.166}$ (prepared in autoclave at 135° C.) | 458.3 | 476.7 | 90 | 167.0 | 45.3 | 45.7 |
| 32 | $V_{1.0}P_{1.15}U_{0.20}O_x + W°_{0.166}$ (prepared in autoclave at 135° C.; prepared using uranylacetate) | 445 | 464.4 | 78.4 | 21.6 | 38.7 | 38.6 |
| 33 | $V_{1.0}P_{1.15}U_{0.20}O_x + W°_{0.166}$ (prepared in autoclave at 135° C.; prepared using uranylacetate) | 445 | 464.4 | 78.4 | 21.6 | 38.7 | 38.6 |
| 34 | $V_{1.0}P_{1.15}U_{0.20}O_x + W°_{0.166}$ (prepared in autoclave at 135° C.; prepared using uranylacetate) | 424.4 | 440.6 | 80 | 147.0 | 46.2 | 48.5 |
| 35 | $V_{1.0}P_{1.15}U_{0.20}O_x + W°_{0.166}$ (prepared in autoclave at 235° C.) | 461.1 | 486.7 | 89 | 19.9 | 41.1 | 41.5 |
| 36 | $V_{1.0}P_{1.15}U_{0.20}O_x + W°_{0.166}$ (prepared in autoclave at 235° C.) | 449.4 | 476.7 | 90 | 114.9 | 42.2 | 41.0 |
| Comp 10 | $V_{1.0}P_{1.15}U_{0.20}O_x$ (prepared using HCl) | 484 | 500 | 97 | 8.0 | 41.2 | 44.6 |
| C-11 | $V_{1.0}P_{1.15}U_{0.20}O_x$ (prepared using HCl) | 484 | 500 | 91 | 107.0 | 41.2 | 44.1 |
| C-12 | $V_{1.0}P_{1.15}U_{0.20}O_x$ (prepared using HCl) | 484 | 506 | 61 | 126.0 | 39.9 | 42.9 |
| C-13 | $V_{1.0}P_{1.15}U_{0.20}O_x$ (prepared using HCl) | 485 | 501 | 84 | 201 | 41.7 | 43.3 |
| C-14 | $V_{1.0}P_{1.15}U_{0.20}O_x$ (HCl duplicate I) | 490.6 | 510 | 76 | 4.9 | 40.2 | 43.3 |
| C-15 | $V_{1.0}P_{1.15}U_{0.20}O_x$ | 487.8 | 507.2 | 75 | 94.7 | 34.0 | 36.0 |

TABLE I-continued

Reaction of n-Butane Using Catalysts Prepared by Invention Compared with Catalysts Prepared by Other Methods

| Example | Catalyst | Temp. °C. Bath | Temp. °C. Bed | Molar Feed Ratio Air/n-Butane | Hours on Stream | Per Pass Conversion, % TA* | Selectivity |
|---|---|---|---|---|---|---|---|
| C-16 | $V_{1.0}P_{1.15}U_{0.20}O_x$ (HCl duplicate I) | 456.1 | 468.3 | 76 | 99 | 37.9 | 50.3 |
| C-17 | $V_{1.0}P_{1.15}U_{0.20}O_x$ (HCl duplicate I) | 483.9 | 501.7 | 74 | 101 | 38.9 | 42.0 |
| C-18 | $V_{1.0}P_{1.15}U_{0.20}O_x$ (HCl duplicate I) | 429.4 | 451.7 | 74 | 120 | 11.5 | 50.0 |
| Comp 19 | $V_{1.0}P_{1.15}U_{0.20}O_x$ (HCl duplicate I) | 445 | 465.6 | 26 | 123 | 27.8 | 52.0 |
| C-20 | $V_{1.0}P_{1.15}U_{0.20}O_x$ (HCl duplicate II) | 480 | 490 | 113 | 2.0 | 53.9 | 53.0 |
| C-21 | $V_{1.0}P_{1.15}U_{0.20}O_x$ (HCl duplicate II) | 484 | 501 | 87 | 20.5 | 48.7 | 50.0 |
| C-22 | $V_{1.0}P_{1.15}U_{0.20}O_x$ (HCl duplicate II) | 482 | 504 | 88 | 93.3 | 37.4 | 39.2 |
| C-23 | $V_{1.0}P_{1.15}U_{0.20}O_x$ (HCl duplicate II) | 485 | 497 | 45 | 99 | 54.9 | 60.0 |
| C-24 | $V_{1.0}P_{1.15}U_{0.20}O_x$ (HCl duplicate II) | 484 | 495 | 44 | 102 | 51.2 | 58.7 |
| C-25 | $V_{1.0}P_{1.15}U_{0.20}O_x$ (HCl duplicate II) | 491 | 505 | 45 | 105 | 48.9 | 53.3 |
| C-26 | $V_{1.0}P_{1.15}U_{0.20}O_x$ (HCl duplicate II) | 489 | 504 | 44 | 108 | 39.5 | 44.9 |
| Comp 27 | $V_{1.0}P_{1.15}U_{0.20}O_x$ (prepared using oxalic acid) | 537 | 537 | 92 | 1.2 | 1.3 | 11.0 |
| C-28 | $V_{1.0}P_{1.15}U_{0.20} + W°_{0.166}$ (low temperature preparation: evaporation with nitrogen stream) | 522.8 | 530.6 | 90 | 138.8 | 27.5 | 30.9 |
| C-29 | $V_{1.0}P_{1.15}U_{0.20} + W°_{0.166}$ (second low temperature preparation) | 546.1 | 546.1 | 87.5 | 3.5 | 13.1 | 30.2 |
| C-30 | $V_{1.0}P_{1.15}U_{0.20} + W°_{0.166}$ (low temperature duplicate) | 554.4 | 554.4 | 92 | 27.9 | 4.6 | 9.5 |
| C-31 | $V_{1.0}P_{1.15}U_{0.20} + W°_{0.166}$ (prepared in autoclave at 110° C.) | 504.4 | 515 | 81 | 3.6 | 17.3 | 31.0 |
| C-32 | $V_{1.0}P_{1.15}U_{0.20} + W°_{0.166}$ (prepared in autoclave at 110° C.) | 535.6 | 545.6 | 81 | 6.3 | 13.9 | 25.5 |
| C-33 | $V_{1.0}P_{1.15}U_{0.20} + W°_{0.166}$ (prepared in autoclave at 110° C.; prepared using colloidal $V_2O_5$) | 468.3 | 486.1 | 88 | 35.8 | 40.4 | 40.9 |
| C-34 | $V_{1.0}P_{1.15}U_{0.20} + W°_{0.166}$ (prepared in autoclave at 110° C.; prepared using colloidal $V_2O_5$) | 463.9 | 482.2 | 85 | 61.9 | 41.1 | 42.4 |
| Comp 35 | $V_{1.0}P_{1.15}U_{0.20} + W°_{0.166}$ (prepared in autoclave at 110° C.; prepared using colloidal $V_2O_5$) | 401.7 | 406.7 | 87 | 81.3 | 27.14 | 55.6 |
| C-36 | $V_1P_1U_{0.20}O_x + W°_{0.166}$ (prepared by preforming $V_2O_5$—$P_2O_5$, then reducing $V^{+5}$) | 518.3 | 522.8 | 94 | 19.0 | 10.2 | 15.4 |

*at least 98% pure maleic anhydride

TABLE II

Reaction of n-Butane Using V—P—O Catalyst

| Example | Catalyst | Temp. °C. Bath | Temp. °C. Bed | Molar Feed Ratio Air/n-Butane | Hours on Stream | Per Pass Conversion, % TA* | Selectivity |
|---|---|---|---|---|---|---|---|
| 37 | $V_{1.0}P_{1.15}O_x + W°_{0.166}$ (autoclaved 135° C.) | 528.3 | 546.1 | 82 | 24.6 | 33.3 | 34.3 |
| 38 | $V_{1.0}P_{1.15}O_x + W°_{0.166}$ (autoclaved 135° C.) | 518.3 | 533.3 | 83 | 27.9 | 36.3 | 38.0 |
| 39 | $V_{1.0}P_{1.15}O_x + W°_{0.166}$ (autoclaved 135° C.) | 518.3 | 533.9 | 85 | 50.6 | 36.6 | 37.3 |
| Comp 37 | $V_{1.0}P_{1.15}O_x$ (HCl digestion) | 499 | 505 | 112 | 6.4 | 30.43 | 54.5 |
| C-38 | $V_{1.0}P_{1.15}O_x + W°_{0.166}$ (evaporation on steam bath) | 485 | 496.1 | 91 | 1.2 | 38.7 | 43 |
| C-39 | $V_{1.0}P_{1.15}O_x + W°_{0.166}$ (evaporation on steam bath) | 510 | 525.6 | 92 | 5.4 | 34.1 | 36 |
| C-40 | $V_{1.0}P_{1.15}O_x + W°_{0.166}$ (duplicate evaporation on steam bath) | 518.3 | 529.4 | 90 | 20 | 34.1 | 39 |
| C-41 | $V_{1.0}P_{1.15}O_x + W°_{0.166}$ (duplicate evaporation on steam bath) | 527.8 | 540. | 90 | 23.8 | 34.7 | 37 |
| C-42 | $VPO_5$ | 537.8 | 537.8 | 89 | 46.0 | 1.22 | 13.4 |

TABLE II-continued

| | | Reaction of n-Butane Using V—P—O Catalyst | | | | |
|---|---|---|---|---|---|---|
| | | Temp. °C. | | Molar Feed Ratio | Hours on | Per Pass Conversion, % |
| Example | Catalyst | Bath | Bed | Air/n-Butane | Stream | TA* Selectivity |
| | ($P_2O_5 + V_2O_5$) | | | | | |

*at least 98% pure maleic anhydride

Examples 40 to 44 and Comparative Examples 43 to 47

Reaction of 2-Butene Using Catalysts Prepared by Invention Compared with Catalysts Prepared by Other Methods The catalyst prepared in Examples 1, Part B, Examples 2 and 3 and in Comparative Example 1, Parts A and C were employed in the oxidation of 2-butene. The results of these experiments appear in TABLE III.

Examples 45 to 60

Reaction of n-Butane Using Various Catalysts Of the Invention

The catalysts prepared in Examples 6 to 20 were employed in the oxidation of n-butane. The results of these experiments appear in TABLE IV.

Examples 61 to 64

TABLE III

Reaction of 2-Butene Using Catalysts Prepared by Invention Compared with Catalysts Prepared by Other Methods

| | | Temp. °C. | | Molar Feed Ratio | Hours on | Per Pass Conversion, % | | |
|---|---|---|---|---|---|---|---|---|
| Example | Catalyst | Bath | Bed | Air/2-Butene | Stream | TA | MAA | Selectivity |
| 40 | $V_{1.0}P_{1.15}U_{0.20}O_x + W°_{0.166}$ (autoclaved 180° C.) | 346.1 | 357.2 | 87 | 129.2 | 41.4 | | 34.4 |
| 41 | $V_{1.0}P_{1.15}U_{0.20}O_x + W°_{0.166}$ (autoclaved 180° C.) | 351.7 | 379.4 | 83 | 241 | 29.3 | | 24.3 |
| 42 | $V_{1.0}P_{1.15}U_{0.20}O_x + W°_{0.166}$ (autoclaved 135° C.) | 401.7 | 450.6 | 58 | 295.8 | 36.2 | | 32.2 |
| 43 | $V_{1.0}P_{1.15}U_{0.20}O_x + W°_{0.166}$ (autoclaved 135° C.; uranyl acetate employed in preparation) | 343.3 | 352.2 | 80 | 169 | 28.1 | | 25.8 |
| 44 | $V_{1.0}P_{1.15}U_{0.20}O_x + W°_{0.166}$ (autoclaved 135° C.; uranyl acetate employed in preparation) | 343.3 | 356.1 | 70 | 210 | 34.82 | | 26.8 |
| Comp 43 | $V_{1.0}P_{1.15}U_{0.20}O_x$ (HCl digestion) | 426 | 483 | 46.7 + 18.8 $H_2O$ | 26.6 | 53.4 | 47.4 | |
| C-44 | $V_{1.0}P_{1.15}U_{0.20}O_x$ (HCl digestion) | 421 | 479 | 47.2 + 19.1 $H_2O$ | 29.0 | 55.9 | 48.3 | |
| C-45 | $V_{1.0}P_{1.15}U_{0.20}O_x$ (HCl digestion) | 421 | 502 | 68.5 | 96.7 | 44.7 | | |
| C-46 | $V_{1.0}P_{1.15}U_{0.20}O_x$ (duplicate II) | 385 | 413 | 68.1 | 3.2 | 55.3 | 42.6 | |
| Comp-47 | $V_{1.0}P_{1.15}U_{0.20}O_x$ (duplicate II) | 385 | 413 | 68.1 | 3.2 | 55.3 | 42.6 | |

Reaction of 2-Butene Using Various Catalysts Of the Invention

Various catalysts prepared in Examples 6 to 20 were employed in the oxidation of 2-butene. The results of these experiments appear in TABLE V.

TABLE IV

Reaction of n-Butane Using Various Catalysts of the Invention

| | | Temp. ° C. | | Molar Feed Ratio | Hours on | Per Pass Conversion, % | |
|---|---|---|---|---|---|---|---|
| Example | Catalyst | Bath | Bed | Air/n-Butane | Stream | TA* | Selectivity |
| 45 | $V_{1.0}P_{1.15}U_{0.20}Ta_{0.05}O_x + W°_{0.166}$ | 511.1 | 532.2 | 76 | 25.1 | 17.77 | 18.1 |
| 46 | $V_{1.0}P_{1.15}U_{0.20}Ce_{0.05}O_x + W°_{0.166}$ | 440.6 | 450 | 84 | 23.3 | 34.67 | 36.7 |
| 47 | $V_{1.0}P_{1.15}U_{0.20}Cr_{0.05}O_x + W°_{0.166}$ | 490.7 | 504.4 | 82 | 23.5 | 12.36 | 32.6 |
| 48 | $V_{1.0}P_{1.15}U_{0.20}Mn_{0.05}O_x + W°_{0.166}$ | 480.6 | 501.1 | 71 | 21.6 | 29.37 | 32.7 |
| 49 | $V_{1.0}P_{1.15}U_{0.20}Co_{0.05}O_x + W°_{0.166}$ | 485 | 495 | 64 | 23.1 | 24.38 | 27.6 |
| 50 | $V_{1.0}P_{1.15}U_{0.20}Cu_{0.05}O_x + W°_{0.166}$ | 493.3 | 508.9 | 57 | 4.8 | 25.03 | 25.0 |
| 51 | $V_{1.0}P_{1.15}U_{0.20}Sb_{0.05}O_x + W°_{0.166}$ | 496.1 | 510 | 61 | 68.1 | 35.84 | 38.5 |
| 52 | $V_{1.0}P_{1.15}U_{0.20}Fe_{0.05}O_x + W°_{0.166}$ | 502.8 | 512.8 | 60 | 20.1 | 11.20 | 16.6 |
| 53 | $V_{1.0}P_{1.15}U_{0.20}Bi_{0.05}O_x + W°_{0.166}$ | 515.6 | 537.8 | 72 | 20.5 | 26.47 | 25.8 |
| 54 | $V_{1.0}P_{1.15}U_{0.20}W_{0.05}O_x + W°_{0.166}$ | 451.7 | 477.8 | 66 | 29.8 | 40.29 | 43.6 |

TABLE IV-continued

Reaction of n-Butane Using Various Catalysts of the Invention

| Example | Catalyst | Temp. °C. Bath | Temp. °C. Bed | Molar Feed Ratio Air/n-Butane | Hours on Stream | Per Pass Conversion, % TA* | Selectivity |
|---|---|---|---|---|---|---|---|
| 55 | $V_{1.0}P_{1.15}U_{0.20}W_{0.05}O_x + W°_{0.166}$ | 454.4 | 482.2 | 64 | 47.6 | 37.48 | 40.7 |
| 56 | $V_{1.0}P_{1.15}U_{0.20}Mo_{0.05}O_x + W°_{0.166}$ | 482.2 | 507.2 | 62 | 95.9 | 28.99 | 33.1 |
| 57 | $V_{1.0}P_{1.15}U_{0.20}(Misch)_{0.05}O_x + W°_{0.166}$ | 489.4 | 506.1 | 74 | 20.4 | 24.68 | 25.2 |
| 58 | $V_{1.0}P_{1.15}U_{0.20}K_{0.02}O_x + W°_{0.166}$ | 471.1 | 488.9 | 66 | 44.4 | 30.79 | 33.1 |
| 59 | $V_{1.0}P_{1.15}U_{0.20}Li_{0.02}O_x + W°_{0.166}$ | 487.8 | 532.2 | 69 | 92.0 | 24.33 | 24.3 |
| 60 | $V_{1.0}P_{1.15}U_{0.20}Ga_{0.02}O_x + W°_{0.166}$ | 476.7 | 506.7 | 73 | 119.2 | 31.95 | 23.9 |

*at least 98% pure maleic anhydride

TABLE V

Reaction of 2-Butene Using Various Catalysts of the Invention

| Example | Catalyst | Temp. °C. Bath | Temp. °C. Bed | Molar Feed Ratio Air/2-Butene | Hours on Stream | Per Pass Conversion, % TA | Per Pass Conversion, % MAA | Selectivity |
|---|---|---|---|---|---|---|---|---|
| 61 | $V_{1.0}P_{1.15}U_{0.20}Ta_{0.05}O_x + W°_{0.166}$ | 371.1 | 384.4 | 69 | 28.4 | 35.06 | | 35.1 |
| 62 | $V_{1.0}P_{1.15}U_{0.20}Ta_{0.05}O_x + W°_{0.166}$ | 372.2 | 381.1 | 66 | 53.6 | 24.12 | | 27.4 |
| 63 | $V_{1.0}P_{1.15}U_{0.20}(Misch)_{0.05}O_x + W°_{0.166}$ | 361.7 | 375.6 | 83 | 24.3 | 35.13 | | 35.1 |
| 64 | $V_{1.0}P_{1.15}U_{0.20}K_{0.02}O_x + W°_{0.166}$ | 360 | 381.1 | 67 | 46.3 | 35.78 | | 35.8 |

We claim:

1. A process for preparing a catalyst comprising the mixed oxides of vanadium and phosphorus, said process comprising the steps of:
    (a) forming an aqueous oxide slurry of a vanadium compound containing pentavalent vanadium and a mineral acid-free, inorganic reducing agent capable of reducing said pentavalent vanadium to a valence state below +5, wherein said reducing agent is selected from the group consisting of a finely divided metal or a colloidal metal;
    (b) admixing a phosphorus compound containing pentavalent phosphorus with said aqueous slurry of step (a);
    (c) heating said aqueous slurry of step (b) at a temperature of at least 120° C. under autogenous pressure so that substantial evaporation of the water in said slurry is prevented;
    (d) removing the water from the slurry of step (c) to form a dried catalyst; and
    (e) calcining the dried catalyst at a temperature of 250° C. to 600° C. in the presence of an oxygen-containing gas.

2. The process of claim 1 wherein said finely divided metal is selected from the group consisting of molybdenum, tungsten, magnesium, aluminum, or nickel.

3. The process of claim 1 wherein the phosphorus to vanadium atom ratio is 0.1:10 to 10:0.1.

4. The process of claim 1 wherein the phosphorus to vanadium atom ratio is 0.5:3 to 3:0.5.

5. The process of claim 1 wherein the compound containing pentavalent vanadium is vanadium pentoxide.

6. The process of claim 1 wherein the compound containing pentavalent phosphorus is phosphoric acid.

7. The process of claim 1 wherein the aqueous slurry of step (c) is heated at a temperature of 120° C. to 300° C.

8. The process of claim 1 wherein the aqueous slurry of step (c) is heated under autogenous pressure of 15 to 1,300 p.s.i.g.

9. The process of claim 1 wherein the aqueous slurry of step (c) is heated at a temperature of 130° C. to 240° C. under autogenous pressure of 20 to 500 p.s.i.g.

10. The process of claim 1 wherein the catalyst is prepared in the absence of a hydrogen halide.

11. The process of claim 1 wherein the catalyst is prepared in the absence of a compound containing trivalent phosphorus.

12. The process of claim 1 wherein the finely divided metal is tungsten.

13. The process of claim 1 wherein said colloidal metal is selected from the group consisting of Mo, W, Mg, Al or Ni.

14. The process of claim 1 wherein the aqueous slurry of step (c) is heated to a temperature of 180° C. to 240° C.

15. A process for preparing a catalyst comprising the mixed oxides of vanadium and phosphorus, said process comprising the steps of:
    (a) refluxing an aqueous oxide slurry containing vanadium pentoxide and a mineral acid-free, inorganic reducing agent capable of reducing the vanadium in the vanadium pentoxide to a valence state below +5 to obtain an aqueous slurry containing reduced vanadium, wherein the reducing agent is selected from the group consisting of a finely divided metal or a colloidal metal;
    (b) admixing phosphoric acid with said aqueous slurry containing reduced vanadium;
    (c) autoclaving the aqueous slurry of step (b) at a temperature of 120° C. to 250° C. under autogenous pressure of 15 to 1300 p.s.i.g. so as to retain substantially all of the water content in the slurry;
(d) removing the water from the slurry of step (c) to form a dried catalyst; and
(e) calcining said dried catalyst at a temperature of 250° C. to 600° C. in the presence of an oxygen-containing gas.

16. The process of claim 15 wherein the finely divided metal is tungsten.

17. The process for preparing a catalyst comprising the mixed oxides of vanadium, phosphorus, and uranium, said process comprising the steps of:
(a) forming an aqueous slurry of a vanadium compound containing pentavalent vanadium and a mineral acid-free, inorganic reducing agent capable of reducing said pentavalent vanadium to a valence state below +5, wherein the reducing agent is selected from the group consisting of a finely divided metal or a colloidal metal;
(b) admixing a phosphorus compound containing pentavalent phosphorus with said aqueous slurry of step (a);
(c) heating said aqueous slurry of step (b) at a temperature of 120° C. under autogenous pressure so that substantial evaporation of the water in said slurry is prevented;
(d) removing the water from the slurry of step (c) to form a dried catalyst; and
(e) calcining the dried catalyst at a temperature of 250° C. to 600° C. in the presence of an oxygen-containing gas;
(f) adding a uranium compound immediately before the addition of the phosphorus compound or after the addition of the phosphorus compound.

18. The process of claim 17 wherein the catalyst prepared is described by the formula $$V_a P_b U_c O_x$$

wherein
a and b are 1 to 10;
c is 0.01 to 5;
x is the number of oxygens required to satisfy the valence requirements of the other elements present;
and wherein
said catalyst optionally contains at least one element selected from the group consisting of tantalum, cerium, chromium, manganese, cobalt, copper, antimony, iron, bismuth, tungsten, molybdenum, alkaline earth metal, an alkali metal, hafnium, zirconium, and thorium.

19. The process of claim 17 wherein the aqueous slurry of step (c) is heated to a temperature of 180° C. to 240° C.

20. The process of claim 18 wherein at least one optional promoter is present in the catalyst in an atomic range of 0.01 to 1.

21. The process of claim 18 wherein a and b are 0.5 to 3.

22. The process of claim 18 wherein c is 0.1 to 0.5.

23. The process of claim 18 wherein the optional promoter is selected from the group consisting of Ta, Ce, Mn, Co, Sb, Fe, Bi, W and Mo.

24. The process of claim 17 wherein the finely divided metal is tungsten in an atomic range of 0.01 to 5.

* * * * *